United States Patent [19]

Guffy et al.

[11] 4,002,721

[45] Jan. 11, 1977

[54] PROCESS IMPROVEMENT IN THE ABSORPTION OF ACID GAS FROM A FEED GAS

[75] Inventors: Joseph C. Guffy, El Cerrito; Robert A. Winkler, Berkeley; Marvin H. Paulson, El Cerrito, all of Calif.

[73] Assignee: Chevron Research Company, San Francisco, Calif.

[22] Filed: Sept. 26, 1974

[21] Appl. No.: 509,507

[52] U.S. Cl. .............................. 423/232; 423/234; 423/226

[51] Int. Cl.² ......................................... B01D 53/34

[58] Field of Search .......... 423/232, 233, 228, 229, 423/226; 55/87; 261/DIG. 26

[56] References Cited

UNITED STATES PATENTS

| | | | |
|---|---|---|---|
| 2,390,899 | 12/1945 | Reed | 423/229 X |
| 2,928,498 | 3/1960 | Schmid-Nisoli et al. | 55/87 |
| 3,100,680 | 8/1963 | Shaw et al. | 423/229 |
| 3,660,016 | 5/1972 | John et al. | 423/226 |

OTHER PUBLICATIONS

Lowry et al., "An Introduction to Organic Chemistry," John Wiley & Sons, Inc., New York, 5th Ed., 1940, page following p. 14.

*Primary Examiner*—Earl C. Thomas
*Attorney, Agent, or Firm*—G. F. Magdeburger; R. H. Davies; D. L. Hagmann

[57] ABSTRACT

In the absorption of an acid gas by an aqueous alkaline solution under gas-liquid absorption conditions, undesirable foaming is reduced by contacting the aqueous solution in a separate contact zone with a hydrocarbon solvent containing an effective amount of an extraction adjuvant.

13 Claims, 1 Drawing Figure

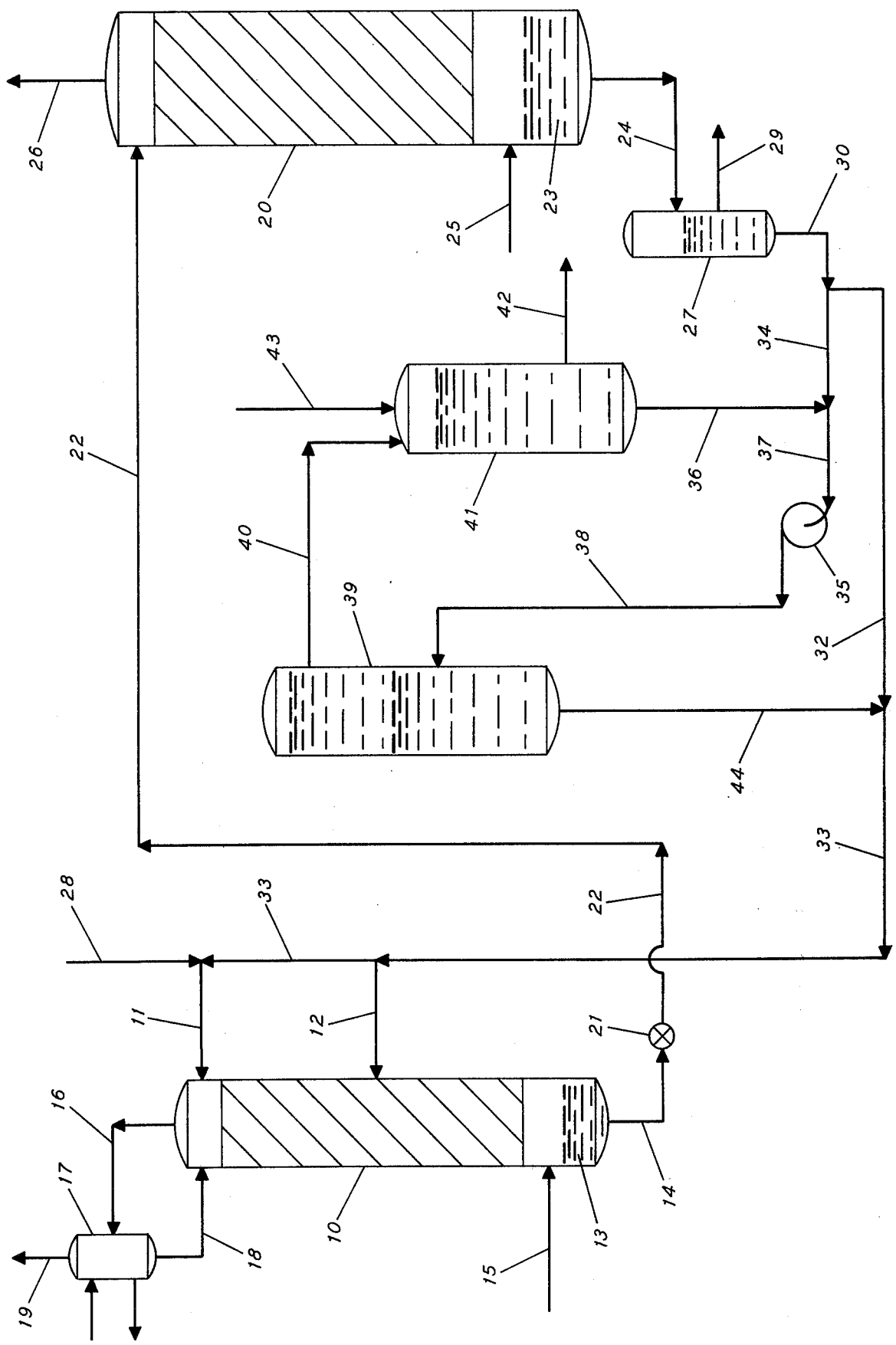

PROCESS IMPROVEMENT IN THE ABSORPTION OF ACID GAS FROM A FEED GAS

BACKGROUND OF THE INVENTION

1. Field of the Invention

This invention relates to an improved process for the absorption of acid gas from a feed gas using an aqueous alkaline solution. more particularly, it relates to a method for reducing undesirable foaming of an aqueous alkaline acidgas absorption solution.

2. Prior Art

The removal of acid gases, principally carbon dioxide and hydrogen sulfide, from gas streams is of considerable industrial importance. Frequently the removal of accomplished by contacting the gas stream with an aqueous alkaline solution and absorbing the acid gas into the solution, stripping the absorbed gas from the solution and regenerating the solution in a separate stage. The thus-regenerated solution is then recycled to the absorption stage. The method is effective, yet not without difficulties. For example, aqueous alkaline solutions have a natural inclination to foam, and the passing of a gas into a foamable solution is classic to the production of a foam. Consequently, resort to the use of anti-foaming agents as additives to the aqueous solution is common practice in the art, as may be noted from U.S. Pat. No. 2,544,564, for example. Nevertheless, excessive foaming, that is foaming in excess of that ordinarily accommodated by the method, is not uncommon. In this event, the excess foaming poses a severe limitation upon the process in that gas flow rates must be substantially reduced to keep the foaming within tolerable limits. In the extreme, the excessive foaming may be akin to a process disaster in that even with a reduction in gas flow a seemingly inexorable flow of foam filling the absorption zone and overflowing into downstream process lines is experienced. The cause of this more-or-less unbridleable foaming appears to be manifold and attributable to not one, but a variety of factors, including compressor lubricating oil condensate, the presence of excess anti-foam agent, and hydrocarbon condensate from the processed gas stream, especially where the source of the gas stream is a petroleum recovery or process stream, and the like. These factors act singly and/or in concert upon the action in the gas absorption and stripping zone. The substantial reduction and/or control of excessive foaming in an acid-gas absorption process is an object of the present invention.

SUMMARY OF THE INVENTION

In accordance with the present invention, excessive foaming is substantially reduced (i.e., by at least about a foam volume reduction of twenty-five percent (25%) in a process for absorbing an acid from a normally gaseous feed comprising the acid gas by contacting the feed with a regenerable alkaline scrubbing solution comprising an aqueous solution containing at least one alkaline acid-gas absorbing agent in a first contact zone under gas-liquid absorption process conditions, including:

1. an excessive foaming of the aqueous solution;
2. withdrawing at least a portion of the contacted solution from the first contact zone; and
3. recycling of the withdrawn solution to the first contact zone, by contacting in a second contact zone at least a portion of the withdrawn solution with a hydrocarbon solvent under liquidliquid extracting conditions, said solvent comprising at least one normally liquid hydrocarbon containing at least 7 carbon atoms and said solvent containing an effective amount of a hydrocarbon-soluble extraction adjuvant, said amount based on 100 parts by weight of the hydrocarbon solvent being in the range from about 2 to 50 parts, and said adjuvant being at least one organic compound composed of carbon, hydrogen and oxygen, having an oxygen-to-carbon atomic ratio which is not greater than about 1:4, respectively, and having a carbon atom content in the range from 4 to about 18.

In a preferred aspect of the present invention, the aforementioned withdrawn aqueous solution is regenerated and then contacted with the adjuvant-promoted hydrocarbon solvent, which is thereafter recycled to the acid-gas contacting zone.

by "acid gas" as used herein is meant normally gaseous acids and normally gaseous oxides which form an acid upon combination of the oxides with water, said acids and resulting acids having standard (25° C. and 1 atmosphere pressure) acid dissociation constants which are less than about 0.1. Representative acid gases include hydrogen sulfide, hydrogen cyanide, carbon dioxide, and the like.

By "excessive foaming" as used herein is meant an incremental foaming by a contaminated scrubbing solution which is at least about 25% of the foaming normally exhibited by the corresponding fresh aqueous alkaline acid-gas scrubbing solution under standard foam test conditions. For this test, a sample of the scrubbing solution is placed in a suitable container, preferably of glass, and a U-type having a flattopped glass-frit gas dispersion (sparger) element as the terminus of one (the shorter) leg of the U-tube, is submerged in the scrubbing solution. The other leg of the tube extends above the liquid level and is attached to a source of nitrogen gas. The U-tube is adjusted in the container so as to provide a distance of 5 centimeters between the surface of the liquid in the container and the top of the gas dispersion element. A foam collection tube 100 cm. in length and having a 25-mm inside diameter is lowered vertically into the solution so as to surround the gas dispersion element to a depth sufficient to insure collection of the generated foam. A suitable means for maintaining the solution at a desired temperature, preferably the temperature of the solution in its use in an acid-gas scrubbing process, a means for stirring the test solution, and a means for determining the distance from the top of the liquid solution and the top of the resulting foam column in the foam collection tube complete the apparatus. In the test, with the solution at temperature, nitrogen gas is introduced into the solution via the gas dispersion element at a rate of 470 cubic centimeters per minute. Five minutes of continuous flow of the nitrogen is in general sufficient to establish the dynamic (standard) foam height for the test solution. When the difference between the standard foam height and the foam height for the contaminated solution is greater than about 25% of the former, excessive foaming is occurring.

PREFERRED EMBODIMENTS

Reference is now made to the accompanying drawing, wherein the FIGURE is a diagrammatic flow sheet illustrating a preferred embodiment of the invention.

Referring now to the FIGURE, the numeral 10 refers generally to a packed absorber column adapted to operate at superatmospheric pressures, for example at a pressure of about 14.5 atmospheres. A packing, such as raschig rings, is desirably charged to the column as a means for producing intimate gas-liquid contacting.

The absorber column is supplied with regenerated and/or regenerated-and-extracted scrubbing solution, such as a recycle stream of aqueous potassium carbonate solution, by lines 11 and 12. The relative amount of the regenerated-and-extracted scrubbing solution desirably present in the recycled scrub solution varies, depending upon the rate of buildup of the condition responsible for the excessive foaming. In extreme, all of the recycled stream is both regenerated and extracted solution. Ordinarily, and where the buildup rate is merely insidious, the recycle stream should contain but a minor portion of the extracted and regenerated solution, for example about 10 volume percent. Alternatively, all or a part of a recycle stream may be intermittently supplied as extracted-and-regenerated scrubbing solution, particularly where an unfortuitous event has resulted in the massive introduction of process-stream contaminants capable of causing excessive foaming. Line 11 delivers a stream of scrubbing solution to the top of the absorber column, and this stream flows over the packing. Line 12 delivers a second stream of scrubbing solution to a central portion of the column, and this stream mixes with that introduced by line 11, and the mixed solution then flows down through the column and collects at the bottom in sump 13 and is removed from the column by line 14.

In general, any regenerable aqueous alkaline scrubbing solution may be employed in the system of the invention. In the present example, wherein the feed is a normally gaseous mixture obtained from a carbon-dioxide-flooded natural gas field, the scrubbing solution is desirably concentrated aqueous potassium carbonate, for example having a concentration by weight in the range 22 to 35% of the carbonate. In addition, the solution should also contain an additive as a promoter for absorption and desorption of acid gas, for example from 2-6 weight percent of diethanolamine.

The acid-gas stream to be purged of its acid-gas content is introduced into the bottom of the absorber column 10 via line 15 and flows upwardly and countercurrent to the decending liquid in the column, exiting at the top of the column through line 16. If desired or necessary, the gas stream leaving the absorber by line 16 is passed through a cooler-condenser 17 where the gas is cooled and the water vapor condensed. The aqueous condensate from condenser 17 may be returned to the top of the absorber by line 18. The purged gas passes out of the cooler-condenser by line 19 for any desired use.

Regeneration of the scrubbing solution is carried out in the regeneration column generally designated by the reference numeral 20. Desirably this column is provided with suitable packing materials, plates and other suitable means for insuring intimate contact between the decending solution and ascending stripping steam introduced at a lower section of the column.

Spent or fat scrubbing solution, containing absorbed acid gas, is withdrawn from sump 13 at the bottom of absorber column 10 via line 14 and conducted to pressure letdown valve 21, where the pressure on the solution is reduced to that prevailing at the top of regeneration column 20. Then the pressurized solution is conducted by line 22 to the top of the regeneration column for introduction therein. The fat solution flows downwardly over packing or trays or the like and countercurrently to upwardly flowing stripping steam. The steam is introduced to column 20 via line 25. The regenerated scrubbing solution is collected in sump 23 at the bottom of the regeneration column. The acid gas which is stripped from the fat scrubbing solution is withdrawn from column 20 via line 26 and the regenerated scrubbing solution is withdrawn via line 24 and passed to surge pot 27. Fresh scrubbing solution as required is introduced into the system via line 28 and a corresponding amount, as required to maintain a satisfactory scrubbing solution inventory for the system, is withdrawn from the surge pot 27 via line 29.

In the present example, the effluent gas stream from a carbon-dioxide-flooded natural gas field contained entrained heavier hydrocarbons. These, together with other impurities, notably compressor lubricating oil and occasional excesses of added anti-foaming agent, contaminated the scrubbing liquid process stream at a rate such that excessive foaming could be controlled by treating about 10% of the recycle scrubbing solution. Accordingly, via line 30 regenerated scrubbing solution is withdrawn from surge pot 27 and 90% of the stream is directly recycled to column 10 via line 32, and the balance is passed via lines 34 and 37 together with hydrocarbon extraction solvent introduced via lines 36 and 37 to pump 35. Desirably the ratio of extraction solvent to scrubbing solution should be at least about 1:9, respectively. The resulting mixture is passed via line 38 to separation vessel 39, where it separates into a lower aqueous phase and an upper hydrocarbon phase, the latter containing impurities extracted from the aqueous scrubbing solution. The separated hydrocarbon phase is withdrawn from vessel 39 via line 40 and delivered to holding vessel 41. As required, hydrocarbon solvent pregnant with impurity is withdrawn from the vessel 41 via line 42 for purification and recycle to the system or discard.

Fresh hydrocarbon solvent is introduced to the system via line 43 and the holding vessel. Preferably this solution is a paraffinic mixture of the jet fuel range, from example of the $C_7$ to $C_{24}$ carbon-atom-number range. In addition, as a solute, the hydrocarbon solvent contains 1-octanol as an extraction adjuvant. The weight ratio of the hydrocarbon solvent to octanol is desirably 9:1, respectively.

Regenerated and extracted scrubbing solution is withdrawn from separator 39 via line 44, and together with regenerated scrubbing solution from line 32 is passed in recycle via line 33 to column 10. In the above-described manner, excessive foaming of the aqueous scrubbing solution is effectively controlled.

Alternatively, the extraction of the regenerated aqueous scrubbing solution may be carried out in a suitable liquid-liquid extractor, for example as described in the "Encyclopedia of Chemical Terminology," Kirk-Othmer, Editors.

Ordinary hydrocarbon solvents, for example refinery cuts, in general are suitable for use in the present invention. Preferably the carbon atom content of the solvent molecule is at least 7. The lower hydrocarbons, for example the hexanes and pentanes, may also be used where the temperature and pressure conditions are sufficient to maintain the solvent in the liquid phase. More preferably the solvent is a paraffinic hydrocarbon mixture of reasonably high carbon atom content, for example $C_{10}$ and higher, in order to minimize loss due to evaporation and to minimize cost for pressure equipment. Representative hydrocarbon solvents include kerosene and other petroleum refinery cuts, xylene solvent mixtures, jet fuel blends, diesel fuel cuts, and the like.

Extraction of an aqueous acid-gas scrubbing medium with a hydrocarbon solvent in the absence of a suitable extraction adjuvant is usually unsatisfactory. Apparently the impurities responsible for excess foaming are moderately polar materials, at least so much so that moderately oxygenated hydrocarbions are effective promoters, adjuvants, for the extraction of these impurities by a hydrocarbon solvent from aqueous acid-gas scrubbing solutions. In general, organic compounds composed of carbon, hydrogen, and oxygen, having a carbon atom content of 4 and above, preferably in the range from 4 to about 18, and having an oxygen-to-carbon atomic ratio which is equal to or less than 1:4, respectively, are satisfactory for use as adjuvants herein. Individual compounds and mixtures of compounds satisfying these requirements may be used to make up the adjuvant. Preferably the adjuvant is an alkanol. Representative kinds of suitable adjuvants include alcohols, ethers and ketones which satisfy the above oxygen-to-carbon requirements, and representative adjuvants include n-butanol, isobutanol, the pentanols, hexanols, 2-ethylhexanol, n-heptanol, 2-octanol, n-octanol, n-octadecanol, methyl butyl ether, methyl butyl ketone, n-methyl hexyl ketone, and the like oxygenated hydrocarbons having an oxygen-to-carbon ratio which is equal to or less than 1 to 4.

The relative amount of adjuvant required for an effective extraction of impurities responsible for excess foaming varies, depending upon the solvent-adjuvant combination and the impurity(s). Ordinarily at least about 1 volume of adjuvant per 100 volumes of hydrocarbon is required for a significant extraction of the impurity. Usually the amount is desirably in the range from about 2 to 20 volumes, and preferably it is from about 5 to 12 volumes of adjuvant per 100 volumes of hydrocarbon solvent. Higher relative amounts may be used and may be needed in special circumstances, but in the main such use is not desirable for reasons of economy and the like.

Usually a satisfactory extraction — once-through basis — is obtained when the volume ratio of extraction solvent to scrubbing solution is in the range from about 0.5 to 15 per 10 volumes of scrubbing solution processed. A higher ratio may be used but, in general, offers no particular advantages and does, of course, involve an increased process burden without corresponding advantages.

The present invention is useful for the reduction and/or elimination of excessive foaming by acid-gas absorbing systems in general in which an aqueous alkaline scrubbing solution is employed. These systems are well known in the art and as contemplated herein of themselves are not new. Representative acid-gas absorbing reagents and/or precursors of the reagents for these solutions include alkali metal hydroxides, carbonates, sulfides, cyanides, and the like. As is well known, the reactions occurring during absorption and regeneration differ, depending upon the particular scrubbing solution employed. In the case of potassium carbonate, the absorption of carbon dioxide produces potassium bicarbonate while regeneration or disproportionation releases carbon dioxide, producing potassium carbonate. As is also well known, the reversal absorption and desorption reactions do not go to completion in either the absorption or regeneration stages, and consequently the scrubbing solution, as circulated, is actually a mixture.

The use of conventional gas-liquid absorption conditions and processes (see, for example, U.S. Pats. Nos. 2,886,405, 3,264,056 and 3,642,430) are contemplated for use herein. In general, these include intimate contacting of an acid gas with a regenerably acid-gas absorption liquid at a temperature and pressure suitable for maintaining the liquid phase. Accordingly, the pressure may vary widely from subatmospheric to superatmospheric and the temperature from about 0° C. to 125° C. and higher.

Ordinary liquid-liquid extraction conditions are contemplated for use herein. In general, these include intimate contacting of two immiscible liquids with each other at a temperature and pressure suitable for maintaining the two liquid phases. Accordingly, the pressure usually ranges from about atmospheric to moderately superatmospheric and the temperature range from just below the boiling point of the lowest boiling of the two liquids to above the freezing points of both of the liquids. Intimate contacting of the liquids may be achieved using a wide variety of absorption columns, spray, baffle, packed, bubblecap, and the like columns. See "Encyclopedia of Chemical Technology", Kirk-Othmer, Second Ed., pp. 741–761. Also, representative contacting means include powered extractors and linemixing by pumping followed by a settler in a separation vessel. The latter is preferred.

Normally gaseous mixtures comprising acid gas are contemplated for use herein. These may vary widely in their compositions, depending upon the particular source. Usually, but not necessarily, the mixture will contain a minor amount of one or more of the acid gases (see definition above) and a major amount of an inert diluent gas, that is of a gas which is not appreciably adsorbed by an aqueous alkaline solution. Representative diluent gases include oxygen, nitrogen, nitric oxide, carbon monoxide, hydrogen, light hydrocarbons such as methane, ethane, propane and butane, and nonexplosive mixtures thereof, for example air, natural gas, and the like. The mixture may also contain a relatively minor amount of a strong acid gas (see, for example, U.S. Pat. No. 2,997,366), for example sulfur trioxide, but such is undesirable because that portion of the alkaline scrubbing reagent involved in chemically absorbing the strong acid gas cannot be regenerated by ordinary means. Consequently, the useful life of the scrubbing solution is reduced by the presence of strong acid gas in a feed stream.

Representative normally gaseous mixtures containing acid gas which are satisfactorily processed herein include natural gas, raw synthesis gas, hydrocarbon partial oxidation product streams, hydrocarbon steam-reforming product streams, shift reaction (carbon monoxide-water) product streams, coke oven gas, producer gas, and the like normally gaseous mixtures.

The regeneration of the acid-gas-pregnant scrubbing solution is ordinarily carried out by any suitable method, for example by heating, reduction of pressure and heating, stripping with steam and/or an inert gas, rectifying and the like of the acid-gas-containing solution. Preferably the regeneration is by stripping, using steam at an elevated temperature, for example in the range from 150° to 200° C. The steam may be obtained from any suitable source, including, for example, reboiler regenerating steam from the aqueous carbonate-scrubbing solution, and the like.

EXAMPLES 1–21

In the following examples representative portions of contaminated aqueous alkaline scrubbing solution taken from a hot carbonate acid-gas removal plant were tested for foam improvement. This plant was being used for removing carbon dioxide and minor amounts of hydrogen sulfide from natural gas obtained from a field which was flooded with carbon dioxide. The natural gas also contained appreciable amounts of higher condensable hydrocarbons and an excessive amount of anti-foam agent. The above-noted contamination had severely interfered with the gas-scrubbing plant operation by causing excessive foaming in the gas scrubbing and regeneration stages of the acid-gas removal process. The foam test and height determinations were made under the standard foam test conditions described above. The results and additional conditions are listed in the table below.

TABLE

| EX. NO. | HYDROCARBON SOLVENT KIND | MLS | ADJUVANT KIND | MLS | MIXING MEANS HAND | MECHANICAL | SETTLING TIME, HR. 0.5 | 1.0 | FOAM HEIGHT, CM. | REMARKS |
|---|---|---|---|---|---|---|---|---|---|---|
| 1 | None | — | None | — | — | — | — | — | 15–19 | As received, mixed and sampled. |
| 2 | " | — | " | — | — | — | — | — | ≅90 | Foam removed and sampled. |
| 3 | " | — | " | — | — | — | — | — | 38–39 | Overhead reflux water from scrubber. |
| 4 | Jet Fuel | | n-Butyl Alcohol | 3 | X | X | | 3–4 | Excellent | |
| 5 | " | 14 | " | 1 | X | | X | | 6–7 | Fair |
| 6 | " | 14 | n-Amyl Alcohol | 1 | X | | X | | 5–6 | Good |
| 7 | " | 14 | n-Hexyl Alcohol | 1 | | X | X | | 6–7 | Good |
| 8 | " | 14 | n-Octyl Alcohol | 1 | X | | X | | 5–6 | Good |
| 9 | " | 14 | " | 1 | | X | X | | 4–5 | Very good |
| 10 | " | 15 | None | — | X | | | X | 6–8 | Good to poor |
| 11 | " | 7.5 | Diacetone Alcohol | 7.5 | | X | X | | 12–13 | Unsatisfactory |
| 12 | " | 14 | n-Hexyl & Diacetone Alcohol | 0.4; 0.6 | | X | | X | 8–9 | Poor |
| 13 | " | 14 | Hexyl Alcohol | 1 | | X | | X | 9–10 | Unsatisfactory |
| 14 | " | 12 | " | 3 | | X | | X | 7–8 | Poor |
| 15 | " | 7.5 | " | 7.5 | | X | | X | 7–8 | Poor |
| 16 | Isooctane | 30 | None | — | X | | X | | 7–8 | Poor |
| 17 | " | 15 | " | — | | | | | 8–9 | Poor |
| 18 | " | 6 | " | — | X | | | X | 50–53 | Unsatisfactory |
| 19 | 350 Thinner | 27 | n-Butyl Alcohol | 3 | X | | X | | 4–5 | Very good |
| 20 | O.P. Naphtha | 27 | " | 3 | X | | X | | 6–9 | Good to poor |
| 21 | Diesel Fuel | 14 | n-Hexyl Alcohol | 1 | | X | X | | 7–8 | Poor |

What is claimed is:

1. In a cyclic process for absorbing acid gas from a normally gaseous feed comprising said acid gas by contacting the feed with a regenerable alkaline scrubbing solution comprising an aqueous solution containing at least one alkaline acid-gas absorbing agent in a first contact zone under gas–liquid absorption process conditions, including:
   1. an excessive foaming of the aqueous solution;
   2. withdrawing at least a portion of said contacted solution from the first contact zone; and
   3. recycling of the withdrawn solution to the first contact zone, the improvement which comprises substantially reducing said foaming by contacting in a second contact zone at least a portion of said withdrawn solution with a hydrocarbon solvent under liquid-liquid extracting conditions, said solvent comprising at least one normally liquid hydrocarbon containing at least 7 carbon atoms and said solvent containing an effective amount of a hydrocarbon-soluble extraction adjuvant, said amount, based on 100 parts by weight of the hydrocarbon solvent, being in the range from about 2 to 50 parts and said adjuvant being at least one organic compound composed of carbon, hydrogen and oxygen, having an oxygen-to-carbon atomic ratio which is not greater than about 1 to 4 and having a carbon atom content in the range from 4 to about 18.

2. A process improvement as in claim 1 further characterized in that prior to said contacting in the second zone said withdrawn solution is regenerated.

3. A process improvement as in claim 1 wherein said acid gas is a component of natural gas.

4. A process improvement as in claim 3 wherein said acid gas comprises carbon dioxide and natural gas obtained from a carbon-dioxide-flooded natural gas field and said scrubbing solution is aqueous potassium carbonate solution.

5. A process improvement as in claim 1 wherein said hydrocarbon solvent comprises a refinery cut.

6. A process improvement as in claim 5 wherein said normally liquid hydrocarbon has a carbon atom content of at least 10.

7. A process improvement as in claim 1 wherein said adjuvant comprises at least one organic compound selected from the group consisting of alkanols, ethers and ketones.

8. A process improvement as in claim 1 wherein said extraction solvent is a mixture of n-butyl-alcohol-promoted jet fuel, said mixture having a ratio of hydrocarbon to alkanol of about 9 to 1, respectively.

9. A process improvement as in claim 2 wherein said contacting of withdrawn solution with hydrocarbon extraction solvent is carried out using a ratio of extraction solvent to scrubbing solution of at least about 1 to 9, respectively.

10. A process improvement as in claim 1 wherein said amount of adjuvant per 100 parts of hydrocarbon solvent is in the range from about 2 to 20 parts.

11. A process improvement as in claim 11 wherein said amount of adjuvant is from about 5 to 12 parts.

12. A process improvement as in claim 1 wherein for each 10 volumes of the scrubbing solution contacted an amount of extraction solvent in the range from about 0.5 to 15 volumes is used.

13. A cyclic process for absorbing at least one acid gas selected from the group consisting of carbon dioxide and hydrogen sulfide from a natural gas feed obtained from a carbon dioxide-flooded natural gas field by contacting the feed with an acid gas absorbing agent comprising aqueous potassium carbonate in a first contact zone under gas-liquid absorption process conditions, including:

1. an excessive foaming of the aqueous solution;
2. withdrawing at least a portion of said contacted solution from the first contact zone; and
3. recycling of the withdrawn solution to the first contact zone, the improvement which comprises substantially reducing said foaming by contacting in a second contact zone at least a portion of said withdrawn solution with a hydrocarbon solvent under liquid-liquid extracting conditions, said solvent comprising at least one normally liquid hydrocarbon containing at least seven carbon atoms and said solvent containing an effective amount of a hydrocarbon-soluble extraction adjuvant, said amount, based on 100 parts by weight of the hydrocarbon solvent, being in the range from about 2 to 50 parts and said adjuvant being at least one alkanol composed of carbon, hydrogen and oxygen, having an oxygen-to-carbon atomic ratio which is not greater than about 1 to 4 and having a carbon atom content in the range from about 4 to 18.

* * * * *

UNITED STATES PATENT AND TRADEMARK OFFICE
CERTIFICATE OF CORRECTION

PATENT NO. : 4,002,721

DATED : January 11, 1977

INVENTOR(S) : Joseph C. Guffy, Robert A. Winkler and Marvin H. Paulson

It is certified that error appears in the above-identified patent and that said Letters Patent are hereby corrected as shown below:

Col. 1, line 9, "more particularly," should read
--More particularly,--.

Col. 1, lines 15-16, "of accomplished" should read
--is accomplished--.

Col. 1, line 57, "acid from" should read --acid gas from--.

Col. 2, line 20, "by" should read --By--.

Col. 2, line 35, "U-type" should read --U-tube--.

Col. 3, line 61, "decending" should read --descending--.

Col. 5, line 12, "hydrocarbions" should read --hydrocarbons--.

Col. 7, Table, Ex. No. 4:
  MLS under HYDROCARBON SOLVENT, "n-Butyl Alcohol"
    should read --27--;
  KIND under ADJUVANT, "3" should read --n-Butyl Alcohol--
  MLS under ADJUVANT, "X" should read -- 3--;
  HAND under MIXING MEANS should read --X--;
  MECHANICAL under MIXING MEANS, "X" should be blank;
  0.5 under SETTLING TIME, HR., should read --X--;
  1.0 under SETTLING TIME, HR., delete "3-4";
  FOAM HEIGHT, CM., "Excellent" should read -- 3-4 --;
  REMARKS should read --Excellent--.

Col. 9, Claim 11, line 1, "claim 11" should read --claim 10--.

Col. 9, Claim 13, line 1, "A cyclic" should read --In a cyclic--

Signed and Sealed this

Third Day of May 1977

[SEAL]

Attest:

RUTH C. MASON
*Attesting Officer*

C. MARSHALL DANN
*Commissioner of Patents and Trademarks*